US006763086B2

United States Patent
Platonov

(10) Patent No.: US 6,763,086 B2
(45) Date of Patent: Jul. 13, 2004

(54) METHOD AND APPARATUS FOR DETECTING BORON IN X-RAY FLUORESCENCE SPECTROSCOPY

(75) Inventor: Yuriy Platonov, Troy, MI (US)

(73) Assignee: Osmic, Inc., Auburn Hills, MI (US)

( * ) Notice: Subject to any disclaimer, the term of this patent is extended or adjusted under 35 U.S.C. 154(b) by 19 days.

(21) Appl. No.: 10/235,355

(22) Filed: Sep. 5, 2002

(65) Prior Publication Data

US 2004/0047446 A1 Mar. 11, 2004

(51) Int. Cl.[7] .............................................. G21K 1/06
(52) U.S. Cl. ........................................ 378/84; 378/49
(58) Field of Search ............................. 378/49, 84, 85

(56) References Cited

U.S. PATENT DOCUMENTS

| 6,396,900 B1 | * | 5/2002 | Barbee et al. | 378/84 |
| 6,449,086 B1 | * | 9/2002 | Singh | 359/361 |
| 6,577,704 B1 | * | 6/2003 | Holz | 378/44 |
| 6,628,748 B2 | * | 9/2003 | Michaelsen et al. | 378/44 |
| 6,643,353 B2 | * | 11/2003 | Verman et al. | 378/84 |

FOREIGN PATENT DOCUMENTS

WO    WO00/75646 A2    12/2000
WO    WO01/02842    1/2001

OTHER PUBLICATIONS

Ricardo, et al., "Improved Analyzer Multilayers for Aluminum and Boron Detection With X–Ray Fluorescence", vol. 40, No. 16, pp. 2747–2754, Jun. 1, 2001.

\* cited by examiner

Primary Examiner—Craig E. Church
Assistant Examiner—Jurie Yun
(74) Attorney, Agent, or Firm—Brinks Hofer Gilson & Lione

(57) ABSTRACT

The present invention consists of a multilayer structure having at least one triad of layers where each of the three layers is a predetermined material. One of the materials is from a group including lanthanum, lanthanum oxide, or lanthanum-based alloys. A second material is disposed between the first material and a third material. The second material is from a group including carbon, silicon, boron, boron carbide or silicon carbide. The third material is from a group including boron or boron carbide. Alternatively, a fourth material is added to further strengthen and increase the water resistance of the multilayer structure. The fourth material is selected from a group including silicon, boron, boron carbide or silicon carbide. The fourth material is disposed between the third layer of multilayer period n and the first layer of multilayer period n–1.

32 Claims, 2 Drawing Sheets

METHOD AND APPARATUS FOR DETECTING BORON IN X-RAY FLUORESCENCE SPECTROSCOPY

BACKGROUND AND SUMMARY OF THE PRESENT INVENTION

The present invention relates to a multilayer structure for reflecting x-ray radiation and an associated method for analyzing the atomic or molecular composition of a sample through x-ray fluorescence spectroscopy.

Multilayer reflectors, or Bragg reflectors, are often utilized for analyzing structures and detecting the absence or presence of particular atomic elements or molecules. This procedure is generally known as x-ray fluorescence spectroscopy. Such a procedure is useful in detecting impurities of minimal amounts present in the sample of interest. For example, x-ray fluorescence spectroscopy is used in the semiconductor industry for detecting impurities in the silicon and germanium wafers that are the foundation of highly-integrated circuits.

In a typical procedure, an x-ray radiation field is guided to a sample, such as a silicon wafer. The impinging radiation induces a fluorescent radiation field, which is incident upon a multilayer or Bragg reflector. The fluorescent radiation field is directed by the multilayer to a measuring or analyzing detector.

The multilayer functions both as a reflective optic and a frequency selector because only fluorescent radiation that satisfies Bragg's equation is reflected. Bragg's equation in general is:

$$n\lambda = 2d \sin \theta, \quad (1)$$

where n is an integral number, A is the wavelength of the initial x-ray radiation field, d is the periodicity of the lattice structure of the multilayer, and $2\theta$ is the angle of diffraction.

Bragg's equation is satisfied naturally for certain types of crystals that have regular lattice structures. However, typical crystals have spacings of a few tenths of a nanometer, and because soft x-rays have wavelengths between 1–10 nanometers, Equation (1) is not satisfied. Consequently, for soft x-ray analyses using Bragg-type reflections, a multilayer reflector is necessary.

A typical multilayer consists of a substrate upon which layers of two different materials are sequentially deposited, forming a period of layers of thickness d. Generally, one of the materials has a high dielectric constant and the other has a low dielectric constant. Upon impinging at that interface between the dielectric constants, approximately $10^{-2}$ to $10^{-3}$ of the incident radiation is reflected. Therefore, a multilayer structure having $10^2$ to $10^3$ layers would theoretically reflect nearly all of the incident radiation. Multilayers have the added advantage of customization, meaning that the d-spacing can be tailored to meet Bragg's equation for different wavelengths of interest. For example, multilayers can be used to determine the boron content of oxygen carrying materials such as borophosphorsilicate, which is routinely used in the semiconductor industry.

Common multilayers consist of molybdenum-boron carbide ($Mo/B_4C$) periods, lanthanum-boron carbide ($La/B_4C$) periods, and lanthanum-boron (La/B) periods. The $Mo/B_4C$ multilayers were considered an improvement over the prior art, but they still rendered the detection of boron impurities problematic. Most importantly, the $Mo/B_4C$ pairing, although optimized for the detection of boron, also features a significant reflectivity at an energy of E=90 eV, which is an emission line of silicon known as the Si-Lα line. This latent reflectivity increases the background signal in certain silicon-containing samples, such as silicon wafers. This limitation hinders the utilization of the $Mo/B_4C$ pairing in the semiconductor industry.

Further developments in the field led to the innovation of $La/B_4C$ and La/B pairings for multilayers. As compared to the $Mo/B_4C$ pairing, the lanthanum-based pairings provided significantly higher reflectivity of the boron emission line of interest, the B-Kα line. Moreover, background noise created from the Si-Lα line was significantly suppressed.

However, the lanthanum-based pairings possess structural particularities that result in damage to the multilayer during normal procedures. For example, the lanthanum-based pairings are structurally soft, which leads to a tendency to break, crack or deform during shaping and mounting procedures. Additionally, the lanthanum-based pairings have low resistivity to water, which makes the cleaning process delicate, time-consuming, and potentially damaging to the optic.

Accordingly, the present invention consists of a device and method for improving the detection of boron through x-ray analysis. The present invention digresses from the espoused theory of multilayer reflectors and introduces a multilayer structure in which the periodic elements arise in groups of three as opposed to the previous pairings of materials. By implementing a three-part periodicity, the present invention retains all of the advantages of the prior art while simultaneously overcoming its limitations.

In particular, the present invention consists of a multilayer structure having at least one triad of layers where each of the three layers is a predetermined material. One of the materials is from a group including lanthanum, lanthanum oxide, or lanthanum-based alloys. A second material is disposed between the first material and a third material. The second material is from a group including carbon, silicon, boron, boron carbide or silicon carbide. The third material is from a group including boron or boron carbide.

In a second embodiment, a fourth material is added to further strengthen and increase the water resistance of the multilayer structure. The fourth material is selected from a group including silicon, boron, boron carbide or silicon carbide. The fourth material is disposed between the third layer of multilayer period n and the first layer of multilayer period n−1, such that throughout n periods, the respective first and third layers are not adjacent.

DETAILED DESCRIPTION OF THE PREFERRED EMBODIMENTS

Figure 1:
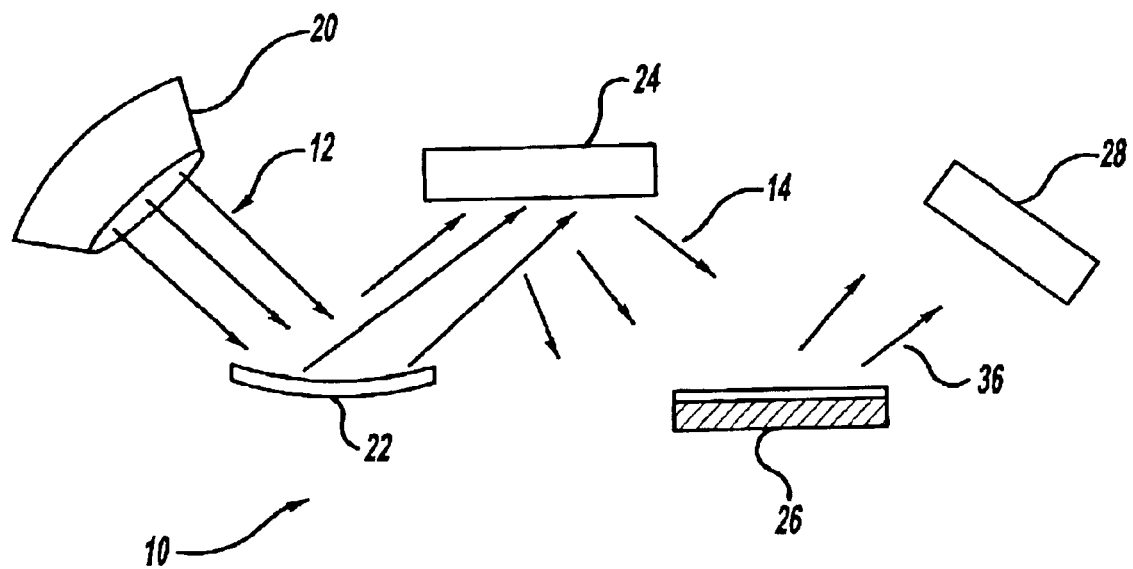
FIG. 1 is a schematic block diagram of the x-ray fluorescence spectroscopy apparatus of the present invention.

In accordance with a preferred embodiment of the present invention, FIG. 1 depicts a system 10 for the x-ray fluorescence analysis of a sample of interest. An x-ray source 20 emits a field of x-ray radiation 12 directed at a reflective optic 22. The reflective optic 22 may be used for collimating or monochromatizing the x-ray radiation 12. Alternatively, the system 10 may operate without the reflective optic 22.

As shown, however, the field of x-ray radiation 12 impinges upon a sample of interest 24, such as a silicon wafer that needs to be analyzed to determine chemical impurities. Due to a known physical reaction between the field of x-ray radiation 12 and the sample 24, a field of fluorescent radiation 14 is emitted from the sample. The field of fluorescent radiation 14 contains information in the form of radiation emission lines about the type of atomic or molecular elements present in the sample 24. The field of fluorescent radiation 14 is selectively reflected from the multilayer structure 26 of the present invention, creating a reflected fluorescent radiation field 36. The reflected fluorescent radiation field 36 is subsequently received and analyzed by a detector 28 that is adapted to interpret qualitative and quantitative aspects of the reflected fluorescent radiation field 36.

Figure 2:
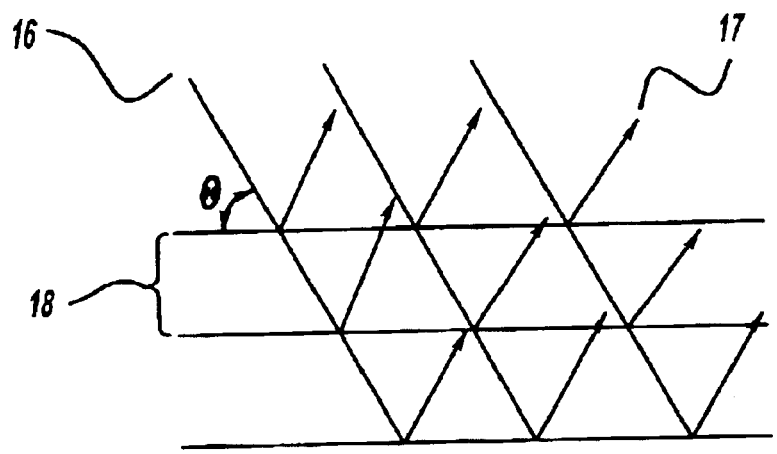
FIG. 2 is a schematic diagram showing the reflection of x-ray radiation from a material satisfying Bragg's equation.

Radiation is selectively reflected from the multilayer structure 26 in accordance with Bragg's equation, Equation 1 above, where a distance d is schematically referred to in FIG. 2 as reference numeral 18. As shown in FIG. 2, incident radiation 16 that impinges upon a surface at an angle θ is reflected at intervals that correspond to the d-spacing 18. Constructive interference between a predetermined number of layers 18 creates a uniform field of reflected radiation 17.

Figure 3:
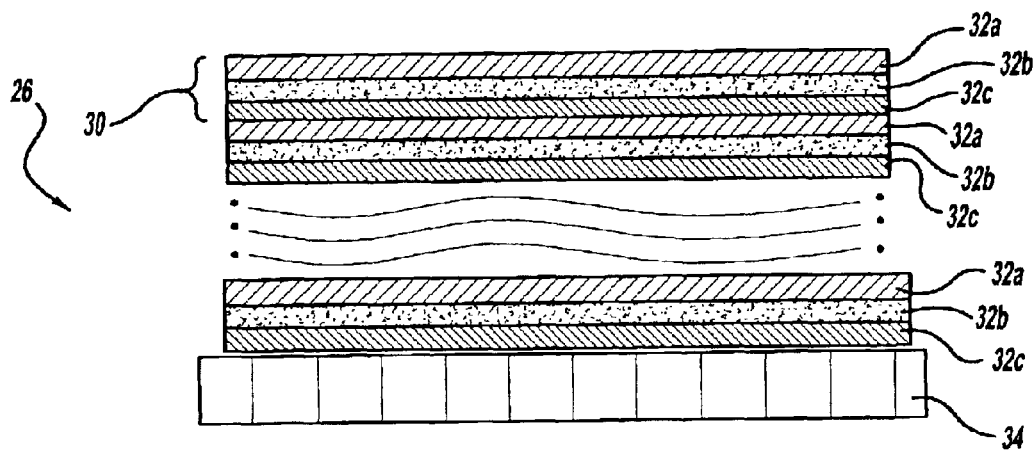
FIG. 3 is a schematic cross-sectional view of a preferred multilayer structure of the present invention having three individual layers.

FIG. 3 depicts a multilayer structure 26 in accordance with a preferred embodiment of the present invention. The multilayer structure 26 generally includes a substrate 34, upon which a series of triadic layers 30 may be periodically formed. As shown, the substrate 34 is planar in nature. However, in alternative embodiments, the substrate 34 may be formed into a curved member. For example, the substrate 34 may be formed into an ellipsoid, a paraboloid, or a spheroid as necessary to accomplish a particular objective.

A series of triadic layers 30 is periodically formed on the substrate 34 to create the multilayer structure 26 of the present invention. Each triadic layer 30 includes a triad of layers 32a, 32b, 32c, which are sequentially deposited upon the substrate 34 to create the necessary periodicity. The multilayer structure 26 is composed of between 1 and 100 triadic layers 30, or between 3 and 300 individual layers 32a, 32b, 32c. In a preferred embodiment, the multilayer structure 26 is composed of between 30 and 60 triadic layers 30, and each triadic layer 30 is between 5 and 60 nanometers in thickness. This thickness is otherwise referred to as the d-spacing of the multilayer structure 26.

As noted, each triadic layer 30 is composed of a triad of layers 32a, 32b, 32c including a first layer 32a, a second layer 32b, and a third layer 32c. Preferably, the first layer 32a is composed of one member from a first group, where the first group includes lanthanum (La), lanthanum oxide ($La_2O_3$), or a lanthanum-based alloy. The second layer 32b is preferably composed of one member from a second group, where the second group includes carbon (C), boron (B), silicon (Si), boron carbide ($B_4C$), or silicon carbide (SiC). The third layer 32c is preferably composed of one member from a third group, where the third group includes boron (B) or boron carbide ($B_4C$). As depicted in FIG. 3, the second layer 32b is preferably disposed between the first layer 32a and the third layer 32c.

Figure 4:
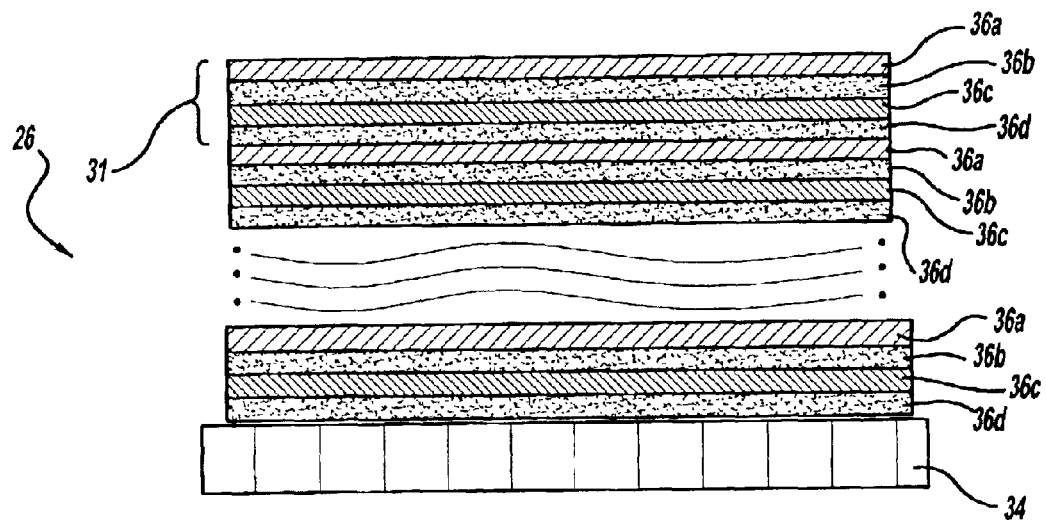
FIG. 4 is a schematic cross-sectional view of a preferred multilayer structure of the present invention having four individual layers.

In a second preferred embodiment of the present invention, shown in FIG. 4, the base period 31 of the multilayer structure 26 includes at least one quartet of layers 36a, 36b, 36c, 36d. A series of quartic layers 31 is periodically formed on the substrate 34 to create the multilayer structure 26 of the present embodiment. Each quartic layer 31 includes a quartet of layers 36a, 36b, 36c, 36d which are sequentially deposited upon the substrate 34 to create the necessary periodicity. The multilayer structure 26 is composed of between 1 and 100 quartic layers 31, or between 4 and 400 individual layers 36a, 36b, 36c, 36d. In a preferred embodiment, the multilayer structure 26 is composed of between 30 and 60 quartic layers 31, and each quartic layer 30 is between 5 and 60 nanometers in thickness. This thickness is otherwise referred to as the d-spacing of the multilayer structure 26.

As noted, each quartic layer 31 is composed of a quartet of layers 36a, 36b, 36c, 36d including a first layer 36a, a second layer 36b, a third layer 36c, and a fourth layer 36d. Preferably, the first layer 36a is composed of one member from a first group, where the first group includes lanthanum (La), lanthanum oxide ($La_2O_3$), or a lanthanum-based alloy. The second layer 36b is preferably composed of one member from a second group, where the second group includes carbon (C), boron (B), silicon (Si), boron carbide ($B_4C$), or silicon carbide (SiC). The third layer 36c is preferably composed of one member from a third group, where the third group includes boron (B) or boron carbide ($B_4C$). The fourth layer 36d is preferably composed of one member from a fourth group, where the fourth group includes carbon (C), boron (B), silicon (Si), boron carbide ($B_4C$), or silicon carbide (SiC).

In a preferred embodiment, the second layer 36b and the fourth layer 36d are chemically identical, although their respective geometrical characteristics will preferably be non-identical. As depicted in FIG. 4, the second layer 36b is preferably disposed between the first layer 36a and the third layer 36c, and the third layer 36c is preferably disposed between the second layer 36b and the fourth layer 36d.

It is a feature of the present invention that the multilayer structure 26 may be shaped or otherwise tailored to maximize the performance of the system 10. For example, the multilayer structure 26 shown in FIGS. 3 and 4 may be shaped into a conic section, such as an ellipsoid, paraboloid, or spheroid in order to regulate the magnitude of the angle of incidence θ at different points on the surface of the multilayer structure 26. By shaping the surface of the multilayer structure 26, the field of fluorescent radiation 14 can be conditioned in a particular manner such that the reflected field of fluorescent radiation 36 is focused upon the detector 28 in a preferred fashion.

Additionally, the d-spacing of the multilayer structure 26 shown in FIGS. 3 and 4, i.e. the thickness of the triadic layer 30 or the quartic layer 31, may be varied along the depth of the multilayer structure 26, or alternatively, along a lateral axis of the multilayer structure 26. The latter manipulations are known as depth graded d-spacing and laterally graded d-spacing, respectively.

The present invention as described in its preferred embodiments thus improves the procedure of x-ray fluorescent spectroscopy by providing a durable multilayer structure with improved spectral resolution, in particular with respect to the fluorescent radiation of boron. In particular, the formation of the multilayer structure composed of triadic or quartic periods greatly increases the overall performance of an x-ray fluorescence spectroscopy system. Both the triadic and quartic periods increase the longevity of the multilayer optic by adding structural integrity to the system, as well as dramatically improved resistance to water.

It should be apparent to those skilled in the art that the above-described embodiments are merely illustrative of but a few of the many possible specific embodiments of the present invention. Numerous and various other arrangements can be readily devised by those skilled in the art without departing from the spirit and scope of the invention as defined in the following claims.

I claim:

1. A multilayer structure for reflecting x-rays comprising:
   at least one triad of layers including a first layer, a second layer, and a third layer;
   wherein the first layer includes one of lanthanum (La), lanthanum oxide ($La_2O_3$), or a lanthanum-based alloy, the second layer includes one of carbon (C), boron (B), silicon (Si), boron carbide (B$_4$C) or silicon carbide (SiC), and the third layer includes one of boron (B) or boron carbide (B$_4$C), and wherein the second layer is disposed between the first layer and the third layer.

2. The multilayer structure of claim 1 wherein the first layer includes one of lanthanum (La) or lanthanum oxide (La$_2$O$_3$).

3. The multilayer structure of claim 1 wherein the third layer consists of boron carbide (B$_4$C).

4. The multilayer structure of claim 1 wherein the second layer includes one of carbon (C), boron (B), or silicon (Si).

5. The multilayer structure of claim 1 wherein the second layer includes one of boron carbide (B$_4$C) or silicon carbide (SiC).

6. The multilayer structure of claim 1 wherein the first layer consists of lanthanum (La), the second layer consists of silicon carbide (SiC), and the third layer consists of boron carbide (B$_4$C).

7. The multilayer structure of claim 1 wherein the first layer consists of lanthanum oxide (La$_2$O$_3$), the second layer consists of silicon (Si), and the third layer consisting of boron carbide (B$_4$C).

8. The multilayer structure of claim 1 wherein the first layer consists of lanthanum oxide (La$_2$O$_3$), the second layer consists of carbon (C) and the third layer consists of boron carbide (B$_4$C).

9. The multilayer structure of claim 1 characterized in that the structure consists of between 1 and 100 of the triads of layers.

10. The multilayer structure of claim 1 characterized in that the structure consists of between 30 and 60 of the triads of layers.

11. The multilayer structure of claim 1 characterized in that the structure is laterally graded.

12. The multilayer structure of claim 1 characterized in that the structure is depth graded.

13. The multilayer structure of claim 1 wherein a thickness of the first layer, a thickness of the second layer, and a thickness of the third layer are substantially identical.

14. The multilayer structure of claim 1 wherein a thickness of the first layer, a thickness of the second layer, and a thickness of the third layer are variable.

15. The multilayer structure of claim 1 characterized in that the structure is elliptically curved.

16. The multilayer structure of claim 1 characterized in that the structure is parabolically curved.

17. The multilayer structure of claim 1 characterized in that the structure is spherically curved.

18. The multilayer structure of claim 1 wherein the at least one triad of layers is between 5 and 60 nanometers in thickness.

19. A method of x-ray fluorescence spectroscopy comprising:

providing a field x-ray radiation;

irradiating a sample to be analyzed with the field of x-ray radiation, thereby inducing a field of fluorescence radiation;

directing the field of fluorescence radiation from a multilayer reflector including at least one triad of layers, the at least one triad of layers including a first layer, a second layer, and a third layer, the first layer including one of lanthanum (La), lanthanum oxide (La$_2$O$_3$), or a lanthanum-based alloy, the second layer including one of carbon (C), boron (B), silicon (Si), boron carbide (B$_4$C) or silicon carbide (SiC), and the third layer including one of boron (B) or boron carbide (B$_4$C).

20. The method of claim 19 further comprising the step of analyzing the field of fluorescence radiation after it has irradiated the sample.

21. An x-ray fluorescence spectroscopy system comprising:

an x-ray source emitting an x-ray radiation field on a sample;

a multilayer structure having at least one period of individual layers, wherein the number of individual layers in the period is either three or four, a first layer including one of lanthanum (La), lanthanum oxide (La$_2$O$_3$), or a lanthanum-based alloy, a second layer including one of carbon (C), boron (B), silicon (Si), boron carbide (B$_4$C) or silicon carbide (SiC), and a third layer including one of boron (B) or boron carbide (B$_4$C);

wherein the sample emits a fluorescent radiation field in response to the x-ray radiation field, and wherein further the multilayer structure selectively reflects the fluorescent radiation field.

22. A multilayer structure for reflecting x-rays comprising:

at least one quartet of layers;

wherein a first layer includes one of lanthanum (La), lanthanum oxide (La$_2$O$_3$), or a lanthanum-based alloy, a second layer includes one of boron (B) or boron carbide (B$_4$C), a third layer includes one of carbon (C), boron (B), silicon (Si), boron carbide (B$_4$C) or silicon carbide (SiC), and a fourth layer includes one of carbon (C), boron (B), silicon (Si), boron carbide (B$_4$C) or silicon carbide (Sic); and wherein the third layer is disposed between the first layer and the second layer, end wherein the second layer is disposed between the third layer and the fourth layer.

23. The multilayer structure of claim 22, characterized in that the structure consists of between 1 and 100 of the quartets of layers.

24. The multilayer structure of claim 22 characterized in that the structure consists of between 80 and 60 of the quartets of layers.

25. The multilayer structure of claim 22 characterized in that the structure is laterally graded.

26. The multilayer structure of claim 22 characterized in that the structure is depth graded.

27. The multilayer structure of claim 22 wherein a thickness of the first layer, a thickness of the second layer, a thickness of the third layer, and a thickness of the fourth layer are substantially identical.

28. The multilayer structure of claim 22, wherein a thickness of the first layer, a thickness of the second layer, a thickness of the third layer, and a thickness of the fourth layer are variable.

29. The multilayer structure of claim 22 characterized in that the structure is elliptically curved.

30. The multilayer structure of claim 22 characterized in that the structure is parabolically curved.

31. The multilayer structure of claim 22 characterized in that the structure is spherically curved.

32. The multilayer structure of claim 22 wherein the at least one quartet of layers is between 5 and 60 nanometers in thickness.

* * * * *

UNITED STATES PATENT AND TRADEMARK OFFICE
CERTIFICATE OF CORRECTION

PATENT NO.     : 6,763,086 B2
DATED          : July 13, 2004
INVENTOR(S)    : Yuriy Platonov It is certified that error appears in the above-identified patent and that said Letters Patent is hereby corrected as shown below:

<u>Column 7,</u>
Line 21, delete "consisting" and substitute -- consists -- in its place.

<u>Column 8,</u>
Line 31, delete "(Sic)" and substitute -- (SiC) -- in its place.
Line 41, after "between" delete "80" and substitue -- 30 -- in its place.

Signed and Sealed this

Thirtieth Day of November, 2004

JON W. DUDAS
*Director of the United States Patent and Trademark Office*